US007207975B2

(12) United States Patent
Miller

(10) Patent No.: US 7,207,975 B2
(45) Date of Patent: Apr. 24, 2007

(54) NEEDLE STICK PROTECTION DEVICE

(76) Inventor: Stuart H. Miller, 16 E. Eighth St., Clifton, NJ (US) 07011-1102

(*) Notice: Subject to any disclaimer, the term of this patent is extended or adjusted under 35 U.S.C. 154(b) by 121 days.

(21) Appl. No.: 10/862,585

(22) Filed: Jun. 8, 2004

(65) Prior Publication Data
US 2005/0182369 A1 Aug. 18, 2005

Related U.S. Application Data

(60) Provisional application No. 60/543,540, filed on Feb. 12, 2004.

(51) Int. Cl.
*A61M 5/32* (2006.01)
(52) U.S. Cl. ............... 604/192; 604/110; 128/919
(58) Field of Classification Search ............. 604/192, 604/198, 187, 263, 110; 128/919
See application file for complete search history.

(56) References Cited

U.S. PATENT DOCUMENTS

| 4,915,702 | A |   | 4/1990  | Haber              |
|-----------|---|---|---------|--------------------|
| 4,917,672 | A | * | 4/1990  | Terndrup et al. ......... 604/192 |
| 5,217,438 | A |   | 6/1993  | Davis et al.       |
| 5,295,972 | A |   | 3/1994  | Mischenko          |
| 5,746,215 | A |   | 5/1998  | Manjarrez          |
| 6,406,459 | B1|   | 6/2002  | Allmon             |
| 6,569,115 | B1|   | 5/2003  | Barker et al.      |
| 6,595,955 | B2| * | 7/2003  | Ferguson et al. ........... 604/110 |
| 2002/0193745 | A1 | | 12/2002 | Ferguson         |
| 2003/0060771 | A1 | | 3/2003  | Bialecki et al.  |
| 2003/0144632 | A1 | | 7/2003  | Hommann et al.   |

* cited by examiner

Primary Examiner—Kevin C. Sirmons
Assistant Examiner—Phillip Gray
(74) Attorney, Agent, or Firm—Welsh + Flaxman LLC

(57) ABSTRACT

A needle stick protection device includes a housing and a locking member positioned within the housing to permit the selective locking of the needle relative to the housing. The locking member includes a spring biased strip having first and second upwardly extending arms connected by a central base member. The first and second upwardly extending arms are biased relative to each other and respectively include a first needle aperture and second needle aperture. A release member is associated with the locking member for facilitating the controlled release of a needle locked in position by the locking member. The release member engages the first upwardly extending arm and the second upwardly extending arm such that selective movement of the release member causes the first and second upwardly extending arms to move between a first locking position and a second release position.

18 Claims, 4 Drawing Sheets

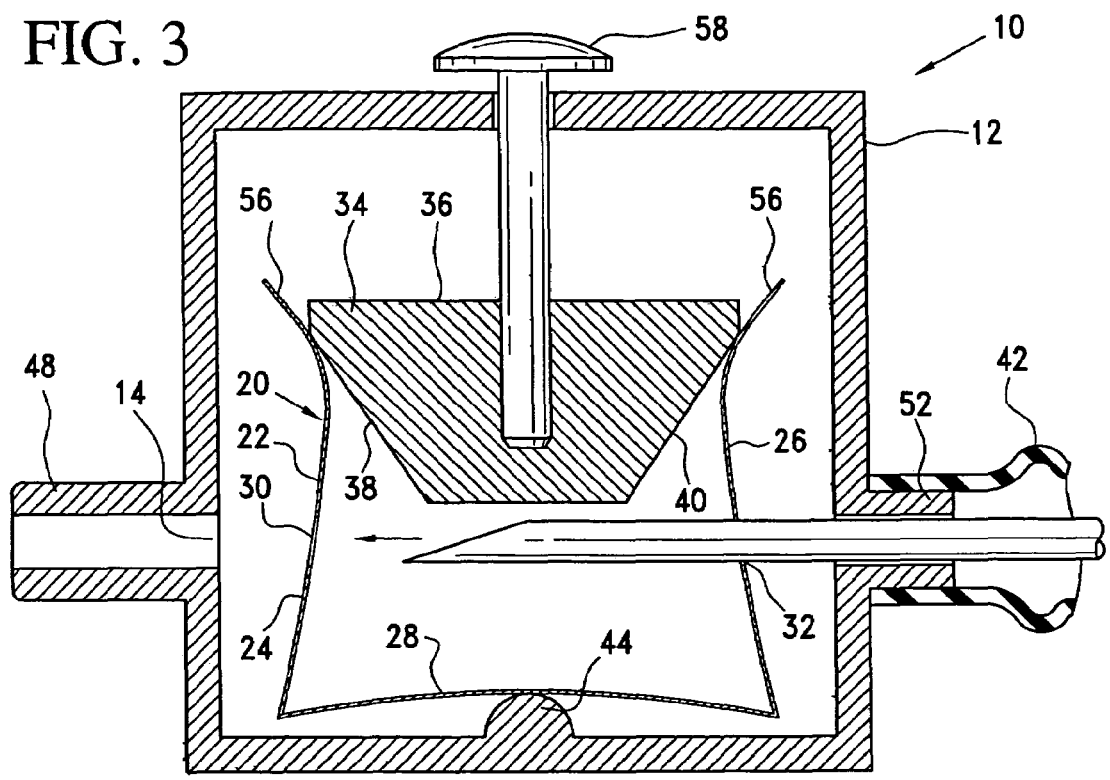
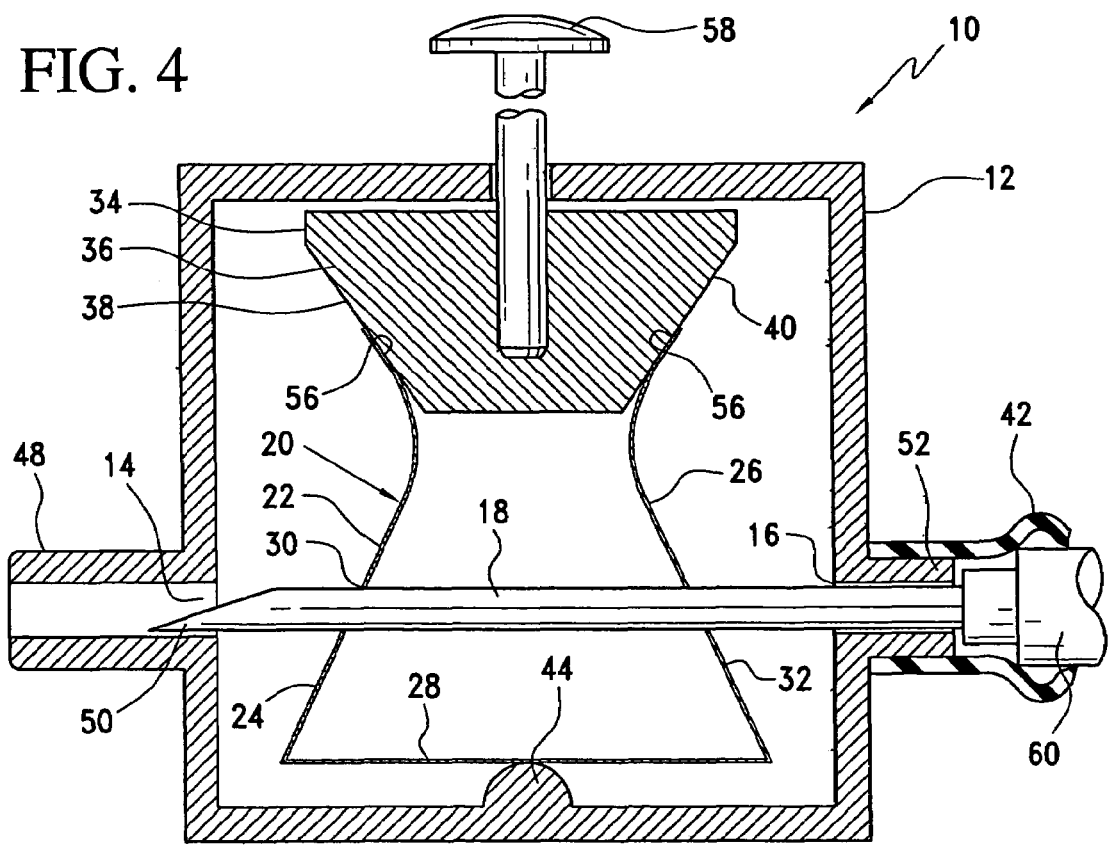

NEEDLE STICK PROTECTION DEVICE

CROSS REFERENCE TO RELATED APPLICATIONS

This application is based upon U.S. Provisional Patent Application Ser. No. 60/543,540, entitled "Needle Stick Protection Device", filed Feb. 12, 2004, which is currently pending.

BACKGROUND OF THE INVENTION

1. Field of the Invention

The invention relates to a device for preventing needle sticks. More particularly, the invention relates to a device for preventing needle sticks wherein the needle may be selectively locked and released within the shielding device.

2. Description of the Prior Art

As those within the medical field have developed an understanding that a variety of diseases may be transferred via unclean and previously used needles, a wide variety of devices have been developed for protecting medical practitioners and other individuals from previously utilized needles.

Currently available needle stick protection devices generally operate by either withdrawing the used needle into a hard protective shell or extending a hard protective shell over the used needle. These devices are utilized once and then discarded in an approved collection device.

While most procedures permit the disposal of needles after a single usage, some medical procedures require that needles be used more than once on a patient. However, these used needles may be passed between physicians and other medical practitioners several times during the procedure and, as such, a possibility exists that physicians and other medical practitioners may be stuck with these contaminated needles during the procedure.

As such, a need exists for a needle stick protection device in which the needle may be selectively shielded and unshielded as the medical procedure dictates. The present invention provides such a needle stick protection device. In fact, the present needle stick protection device may be locked on to the needle at any axial location and can, therefore, act as a stop, limiting the depth of penetration of the needle into the patient and making reinsertion of the needle to the selected depth less time consuming.

SUMMARY OF THE INVENTION

It is, therefore, an object of the present invention to provide a needle stick protection device. The device includes a housing and a locking member positioned within the housing to permit the selective locking of the needle relative to the housing. The locking member includes a spring biased strip having first and second upwardly extending arms connected by a central base member. The first and second upwardly extending arms are biased relative to each other and respectively include a first needle aperture and second needle aperture. A release member is associated with the locking member for facilitating the controlled release of a needle locked in position by the locking member. The release member engages the first upwardly extending arm and the second upwardly extending arm such that selective movement of the release member causes the first and second upwardly extending arms to move between a first locking position in which the first and second upwardly extending arms are angled relative to each other and a second release position in which the first and second upwardly extending arms are substantially parallel. In use, the first and second needle apertures are oriented to permit the free passage of a needle therethrough when the locking member is in its second release position and the first and second needle apertures are oriented to lock the needle relative to the locking member when the first and second upwardly extending arms are in their first locking position.

It is also an object of the present invention to provide a needle stick protection device wherein the housing includes first and second apertures shaped and positioned for permitting the free passage of a needle through the housing.

It is another object of the present invention to provide a needle stick protection device wherein the housing includes a tip shield extending adjacent the first aperture of the housing.

It is a further object of the present invention to provide a needle stick protection device including a bellows seal extending adjacent the second aperture of the housing.

It is also another object of the present invention to provide a needle stick protection device wherein the release member includes a camming member extending between the first upwardly extending arm and the second upwardly extending arm.

It is yet another object of the present invention to provide a needle stick protection device wherein the camming member includes a first tapered side and a second tapered side respectively engaging the first upwardly extending arm and the second upwardly extending arm.

It is also a further object of the present invention to provide a needle stick protection device wherein the release member includes a release button facilitating movement of the release member.

It is still another object of the present invention to provide a needle stick protection device wherein the release member includes a release button facilitating movement of the release member.

It is also an object of the present invention to provide a needle stick protection device wherein the locking member is a metallic strip biased toward the first locking position.

It is another object of the present invention to provide a needle stick protection device wherein the locking member is coupled to a bottom of the housing.

It is a further object of the present invention to provide a needle stick protection device wherein the locking member is coupled to at least one projection along a bottom of the housing.

It is still a further object of the present invention to provide a needle stick protection device wherein the locking member is positioned on a pair of pins.

It is also an object of the present invention to provide a needle stick protection device wherein the locking member is substantially delta shaped when in its first locked position.

It is a further object of the present invention to provide a needle stick protection device wherein the housing includes a tip shield.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 3 is a cross section view with the needle stick protection device in its release position.

FIG. 4 is a cross section view of the needle stick protection device in its locking position.

DESCRIPTION OF THE PREFERRED EMBODIMENTS

Figure 1:
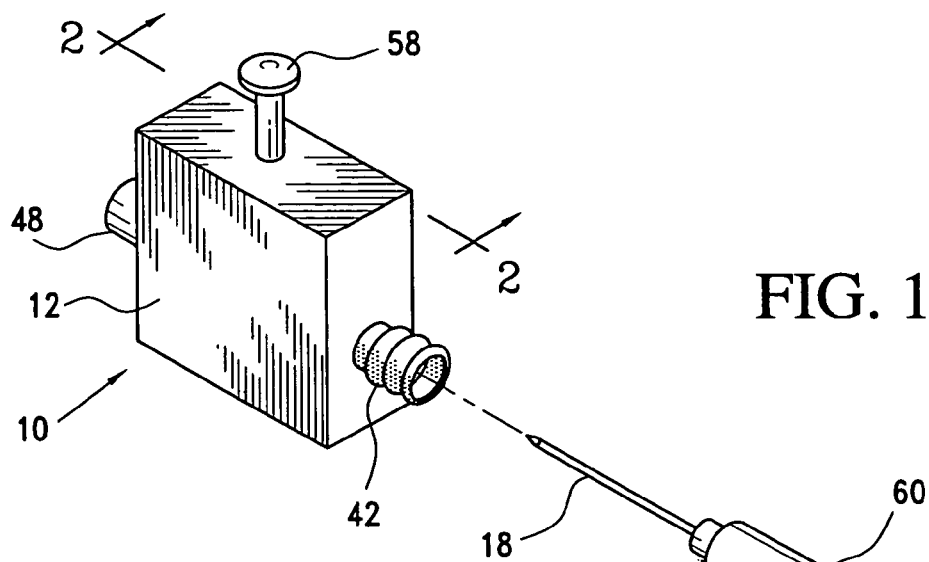
FIG. 1 is an exploded perspective view of the present needle stick protection device.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 5, a needle stick protection device 10 is disclosed. The protection device 10 includes a housing 12 having first and second apertures 14, 16 shaped and dimensioned for permitting the free passage of a needle 18 through the housing 12. The protection device 10 further includes a locking member 20 positioned within the housing 12 to permit the selective locking of the needle 18 relative to the housing 12. The locking member 20 includes a spring-biased strip 22 having first and second upwardly extending arms 24, 26 connected by a central base member 28. The first and second upwardly extending arms 24, 26 are biased toward each other and respectively include a first needle aperture 30 and a second needle aperture 32.

The protection device 10 also includes a release member 34 associated with the locking member 20 for facilitating the controlled release of a needle 18 locked in position by the locking member 20. The release member 34 includes a camming member 36 extending between the first upwardly extending arm 24 and the second upwardly extending arm 26. The camming member 36 includes a first tapered side 38 and a second tapered side 40. The first and second camming surfaces 38, 40 respectively engage the first upwardly extending arm 24 and the second upwardly extending arm 26 such that selective movement of the camming member 36 causes the upwardly extending arms 24, 26 to move between a first locking position (see FIG. 4) in which the first and second upwardly extending arms 24, 26 are angled toward each other and a second release position (see FIG. 3) in which the first and second upwardly extending arms 24, 26 are substantially parallel.

In use, the first and second needle apertures 30, 32 are oriented to permit the free passage of a needle 18 therethrough when the locking member 20 is its second release position and the first and second needle apertures 30, 32 are oriented to lock the needle 18 relative to the locking member 20 when the first and second upwardly extending arms 24, 26 are in the first locking position. The locking member 20 is shaped and dimensioned to fix the position of the needle stick protection device 10 at any axial location along the length of the needle 18. The housing 12 acts to prevent bodily contact with the tip of the needle 18 when the tip of the needle 18 is positioned within the housing 12. The release member 34 is utilized in shifting the locking member 20 to its second release position, unlocking the needle stick protection device 10 so that the needle 18 may slide to any axial location along the length of the needle 18. Finally, and as will be discussed below in greater detail, the protection device 10 includes a bellows seal 42 adapted to prevent bodily contact with the portion of the needle 18 positioned directly behind the housing 12 and to prevent the needle stick protection device 10 from sliding off the end of the needle 18.

In accordance with a preferred embodiment of the present invention, the locking member 20 is a substantially U-shaped, bent metallic strip 22. While a metallic strip is disclosed in accordance with a preferred embodiment of the present invention, other materials may be used while remaining within the spirit of the present invention. As such, the locking member 20 includes a central base member 28 with first and second upwardly extending arms 24, 26. The first and second arms 24, 26 respectively include centrally located first and second needle apertures 30, 32. As will be better appreciated based upon the following disclosure, the apertures 30, 32 are shaped to be slightly larger than the needle 18 intended to pass therethrough. As such, when the first and second arms 24, 26 are close to parallel, the needle may freely slide within the first and second needle apertures 30, 32. However, when the first and second arms 24, 26 are moved toward each other and angled, the diameter of the first and second needle apertures 30, 32 perpendicular to the longitudinal axis of the needle 18 passing therethrough decreases, locking the needle 18 in position. More specifically, the metallic strip 22 is bent in the form of an open delta, that is, a substantially triangular shape with an open apex, including first and second upwardly extending arms 24, 26 connected by the central base member 28.

As mentioned above, the central base member 28 integrally links the first and second upwardly extending arms 24, 26. The apex of the delta forms an opening to accommodate positioning of the release member 34 therebetween in a manner that will be discussed below in greater detail.

In practice, the locking member 20 is biased toward a delta configuration such that the needle stick protection device 10 is locked on to the needle 18 at all times except when the release member 34 is activated to move the first and second upwardly extending arms 24, 26 to a substantially parallel position. More specifically, the needle locking force is provided by the bending induced in the metallic strip 22 when the needle 18 is positioned within the first and second needle apertures 30, 32 and the release member 34 is unactuated.

Figure 2:
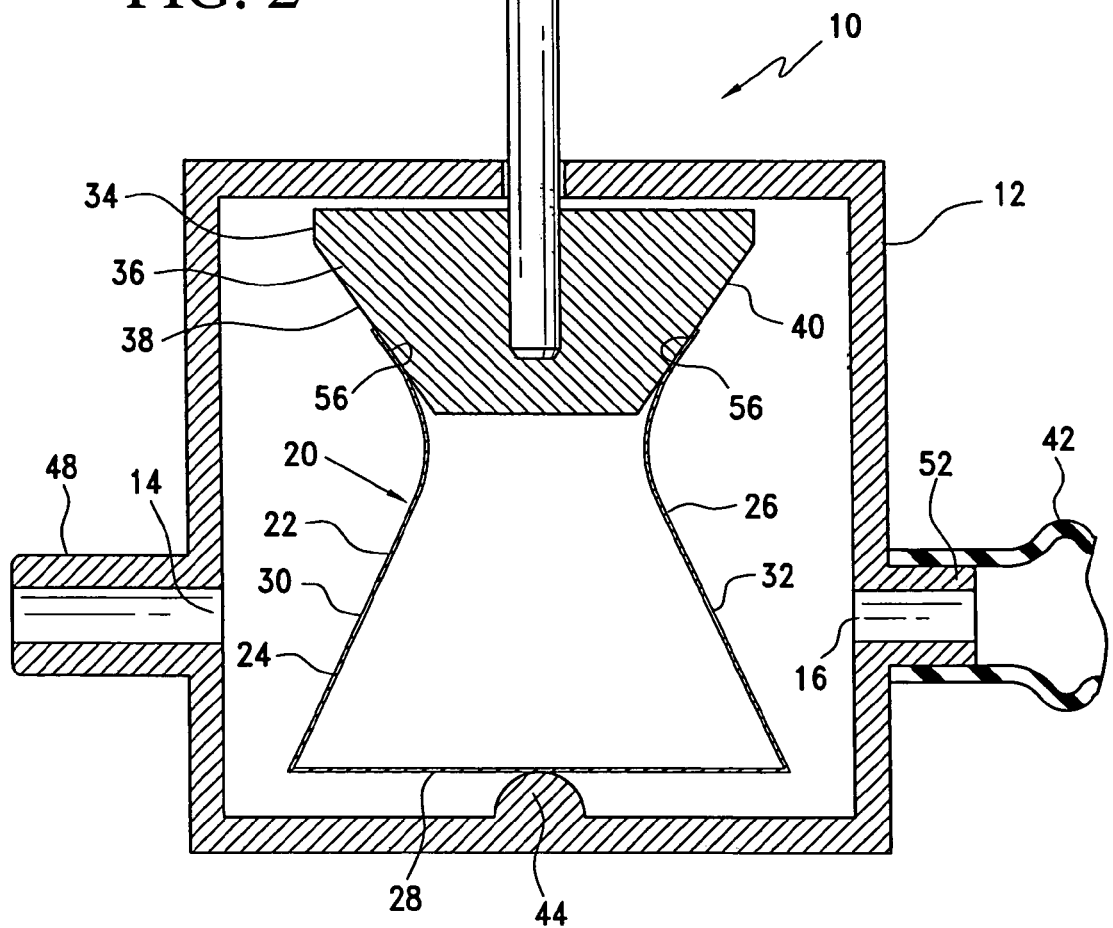
FIG. 2 is a cross section view of the needle stick protection device without the needle.
Figure 5:
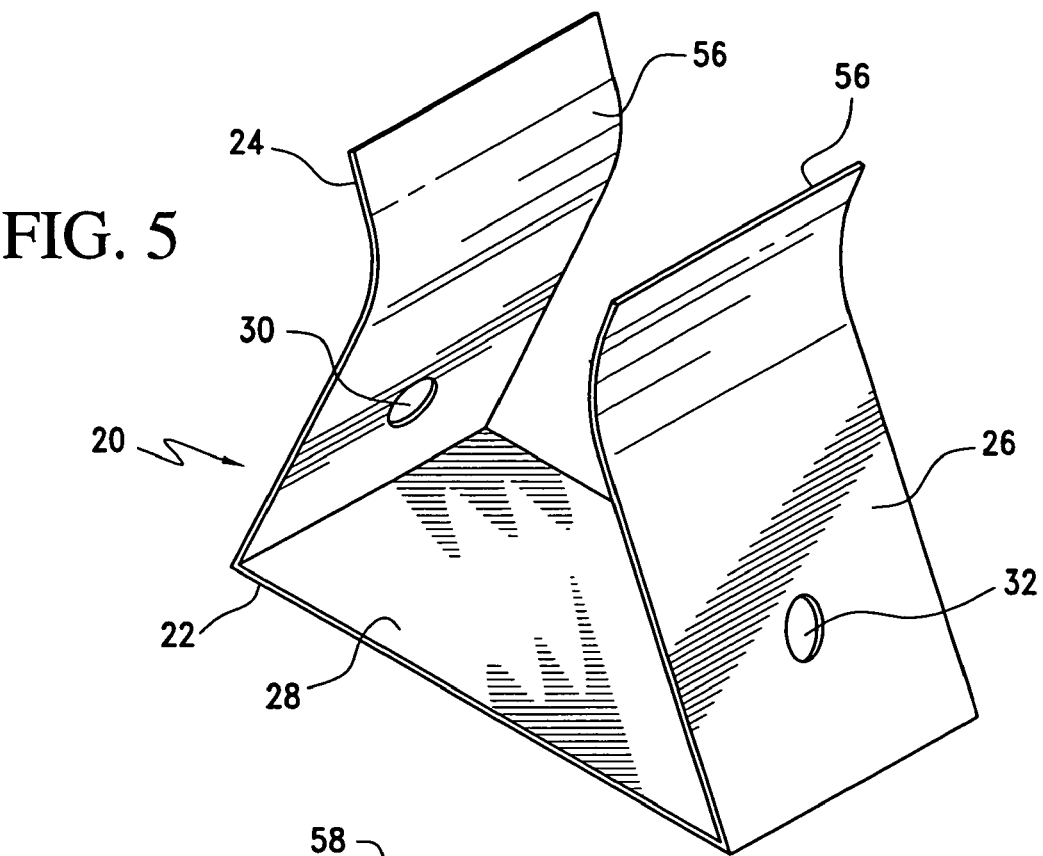
FIG. 5 is a perspective view of the locking member.
Figure 7:
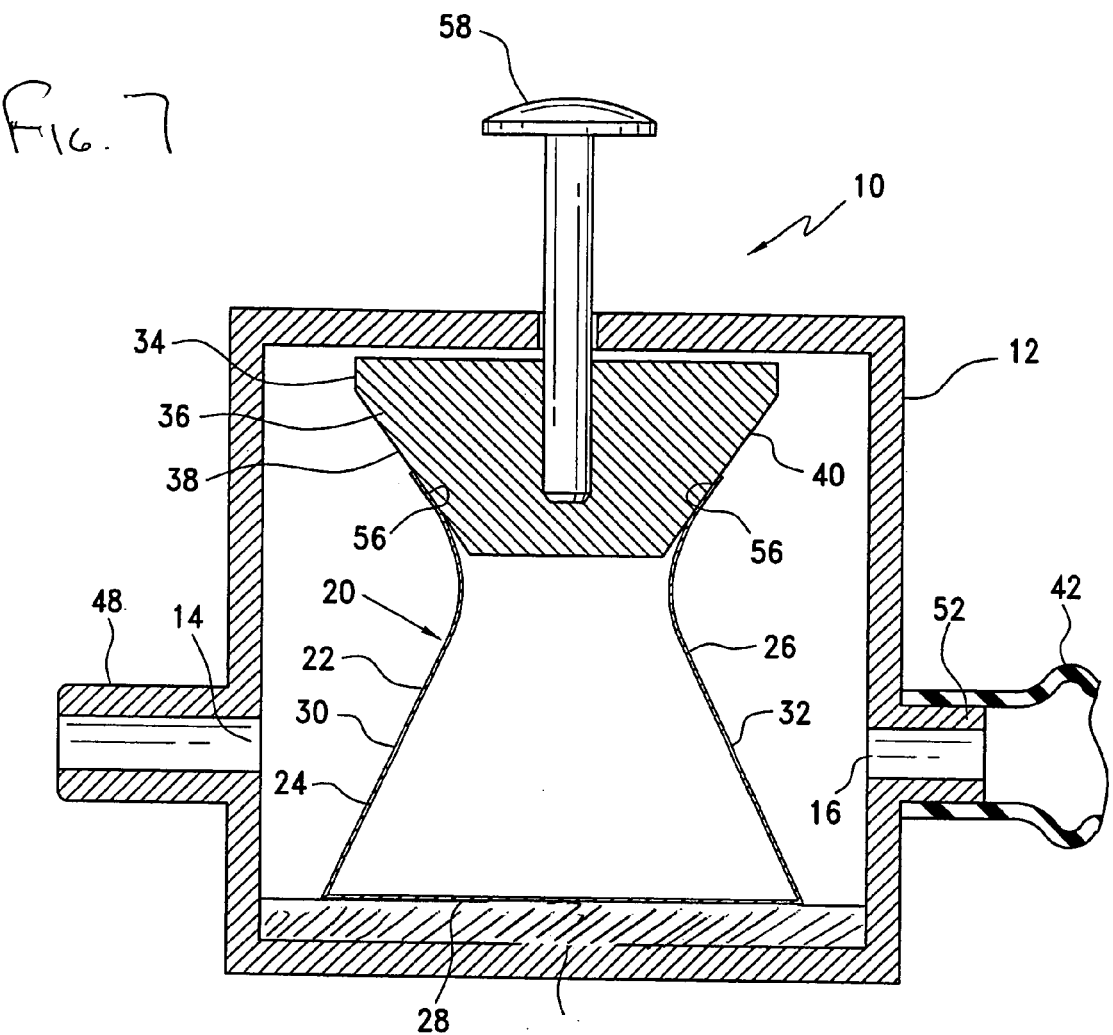
FIG. 7 is a cross sectional view of a needle stick protection device according to another alternate embodiment.

Functioning of the locking member 20 is further enhanced by the coupling of the metallic strip 22 to a projection 44 on the bottom of the housing 12. In accordance with an alternate embodiment, and as shown in FIG. 7, the metallic strip 22 may be supported along the entire length of the lower portion of the housing 12. By fixing the locking member 20 to the projections 44 as shown in FIGS. 2, 3 and 4, the finger pressure required to actuate the release member 34 for release and movement of a needle 18 along the protection device 10 is reduced. However, the projections 44 similarly reduce the resulting contact pressure between the needle 18 and the locking member 20.

Fixing the locking member 20 along the entire length of the lower portion of the plastic housing 12 increases the finger pressure required to actuate the release member 34 and relocate the needle stick protection device 10 along a needle 18 and also increases the contact pressure between the needle 18 and the locking member 20, thereby enhancing the locking force on the needle 18.

Figure 6:
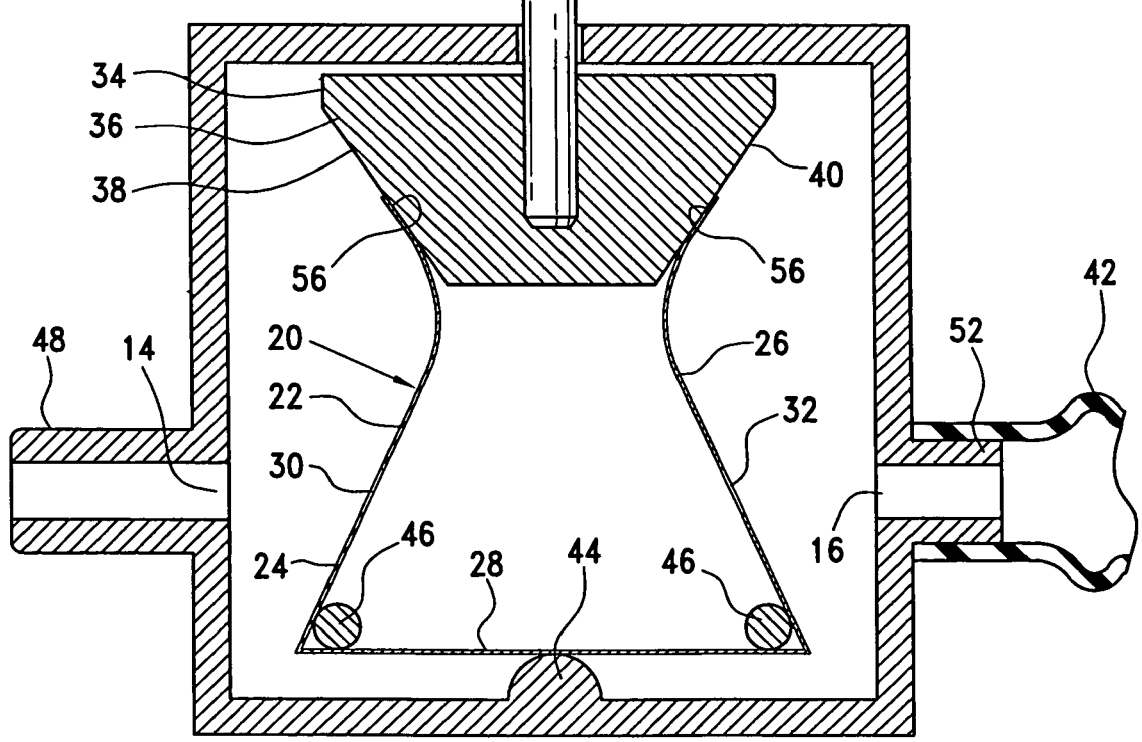
FIG. 6 is a cross sectional view of a needle stick protection device according to an alternate embodiment.

With reference to FIG. 6, it is further contemplated that the locking member 20 may be positioned on two pins 46 rather than only coupling the locking member 20 to the projections 44 as described above with regard to FIGS. 2, 3 and 4. However, and as those skilled in the art will certainly appreciate, there are a variety of ways in which the locking member may be mounted within the housing without departing from the spirit of the present invention.

As mentioned above, the protection device 10 further includes a housing 12 in which the operating components are maintained. The housing 12 is preferably constructed of molded plastic, although other material constructions may be employed without departing from the spirit of the present invention. In accordance with a preferred embodiment, the housing 12 is shaped and dimensioned for maintaining the locking member 20 and release member 34 therein. In addition, the housing 20 is provided with first and second apertures 14, 16 shaped and positioned for permitting the free passage of a needle 18 therethrough.

The housing 12 is further provided with a needle tip shield 48 composed of a tubular portion secured at one end of the housing member 12. The tip shield 48 shields a needle tip 50 without requiring that the needle 18 be pulled fully toward the center of the housing 12. The housing 12 further includes a bellows seal 42 at the opposite end. The bellows seal 42 is secured to a projection 52 extending adjacent the second aperture 16 of the housing 12. Shielding of the needle tip 50 is affected by sliding the needle stick protection device 10 as far as possible toward the tip 50 of the needle 18. The length of the inextensible bellows seal 42 controls the amount of sliding. When the bellows seal 42 is fully extending, the tip 50 of the needle 18 is inside the tip shield 48 of the housing 12 as shown in FIG. 4. The inside diameter of the tip shield 48 of the housing 12 is only slightly larger than the outside diameter of the needle 18. The length of the tip shield 48 is such that body contact with the tip 50 of the needle 18 is impossible.

With regard to the release member 34, it is preferably a low friction, tapered plastic member. The release member includes a camming member 36 having tapered sides 38, 40 shaped and dimensioned for engaging camming surfaces 56 of the first and second upwardly extending arms 24, 26 of the locking member 20. The camming member 36 is coupled to a release button 58. The release button 58 extends through the upper surface of the housing 12 for engagement by a user of the present needle stick protection device 10.

In use, the release member 34 functions to disengage a needle 18 from the locking member 20 by forcing the camming member 36 to increase the size of the open end of the delta of the locking member 20. The camming member engages the first upwardly extending arm 24 and the second upwardly extending arm 26 such that selective movement of the release member 34 causes the first and second upwardly extending arms 24, 26 to move between a first locking position in which the first and second upwardly extending arms 24, 26 are angled toward each other and a second release position in which the first and second upwardly extending arms 24, 26 are substantially parallel. More particularly, the geometry of the camming member 36 is such that the first and second upwardly extending arms 24, 26 of the locking member 20 approach parallelism as the release member 34 is forced downwardly in a manner extending the open end of the delta of the locking member 20. When a substantially parallel configuration is achieved, the needle 18 is free to slide within the first and second needle apertures 30, 32 of the first and second upwardly extending arms 24, 26.

As mentioned above, the housing 12 is provided with a bellows seal 42 that controls the extension of the housing 12 along the length of the needle 18. The bellows seal 42 is preferably composed of a thin, elastomeric tear resistant material. The bellows seal 42 is fastened to the housing 12 of the needle stick protection device 10 adjacent the second aperture 16 such that it extends between the needle protection device 10 and the syringe body 60. The bellows seal 42 is made inextensible by embedding inextensible cords therein. The cords limit the amount of movement the bellows seal 42 can attain. The bellows seal 42 prevents bodily contact with the portion of the needle 18 between the housing 12 and the syringe 60 while simultaneously providing sufficient axial travel to shield the tip 50 of the needle 18 against bodily contact. Although inextensible cords are described in accordance with a preferred embodiment of the present invention, those skilled in the art will appreciate that other structures may be employed without departing from the spirit of the present invention.

In operation, the needle stick protection device 10 is operated by squeezing the release button 58 and the bottom of the housing 12 between the thumb and forefinger. The camming member 36 of the release member 34 thereby forces the first and second upwardly extending arms 24, 26 toward a substantially parallel configuration, that is, toward a release position. By squeezing the needle stick protection device 10 in this manner the projected areas of the first and second needle apertures 30, 32 in planes perpendicular to the needle 18 are varied. Releasing the release button 58 removes the load on the locking member 20 and the locking member 20 attempts to return to its unloaded geometry, presenting a projected area to the needle 18 which is smaller than the transverse cross section of the needle 18 thereby "locking" the needle 18 in place. By varying the projected area of the first and second needle apertures 30, 32 in this manner, the needle stick protection device 10 can be made to lock and unlock the needle 18. Various design equations applied to the present invention allow the user to design a needle stick protection device for a selected needle outer diameter or for a range of needle diameters.

Since the needle stick protection device 10 is locked on to the needle 18 except when the release button 58 is depressed, the needle stick protection device 10 can also be used to limit the depth of needle penetration into the patient by moving the needle stick projection device 10 so that the desired needle length is exposed.

The needle stick protection device 10 is attached to the needle 18 by fully depressing the release button 58 and sliding the housing 12 over the needle 18. Fully depressing the release button 58 lines up the first and second needle apertures 30, 32 and the first and second apertures 14, 16 of the housing 12 so that the needle 18 can be inserted within the first and second apertures 14, 16, the first and second needle apertures 30, 32 and the housing 12. When the release button 58 is released, the locking member 30 attempts to return to its unloaded geometry. Since the transverse cross sectional area of the needle 18 is greater than the minimum projected area of the first and second needle apertures 30, 32 of the locking member 20, the locking member 20 cannot fully return to its unloaded geometry and instead, contacts the needle 18 at four locations. The contact force of the needle 18 with the locking member 20 is a function of the amount of bias remaining in the locking member 20 after the release button 58 is released. The contact force creates friction making it highly difficult for the needle 18 to be moved within the housing 12.

As those skilled in the art will appreciate, various design equations can be used to design a needle stick protection device 10 which will generate any desired contact force. Once the needle stick projection device 10 has been locked on to the needle 18 it remains at that location until the release button 58 is depressed and the needle stick protection device 10 is moved to a new location.

When a medical practitioner desires needle stick protection, the protection device 10 is moved toward the tip 50 of the needle 18 to the limit provided by the elastomeric bellowed seal 42. At this location, the needle tip 50 is inside the tip shield 48 of the housing 12 and bodily contact is impossible. Limited penetration depth into a patient is achieved by moving the needle stick protection device 10 until a desired needle length is exposed. Thereafter, the release button 58 is released. The needle stick protection device 10 is fixed at that location and will limit the depth of penetration by making contact with the patient.

Figure 8:
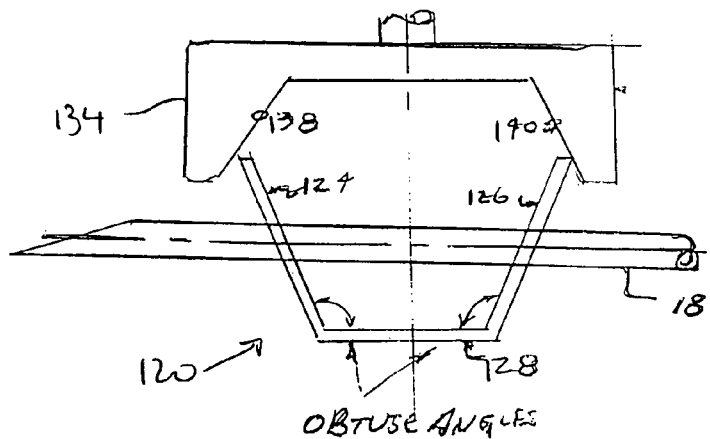
FIG. 8 is a cross sectional view of a needle stick protection device according to still a further alternate embodiment.

The locking member 20 described above is in the form of an open delta. As a result, the angles between the central base member 28 and the first and second upwardly extending arms 24,26 are acute, i.e., the angles are less than 90 degrees. In accordance with an alternate embodiment, and with reference to FIG. 8, the locking member 120 may have obtuse angles between the central base member 128 and the first and second upwardly extending arms 124, 126, i.e., the angles are greater than 90 degrees. In accordance with this embodiment, the resulting geometry of the locking member 120 is in the form of an open channel in which the distance between the ends of the first and second upwardly extending arms 124, 126 is greater than the length of the central base member 128. The release member 134 is similarly shaped with inwardly facing tapered sides 138, 140 shaped and dimensioned for engaging the first and second upwardly extending arms 124, 126 as discussed above with regard to the earlier embodiments.

Although the needle stick protection device herein is directed primarily to the medical field, those skilled in the art will appreciate that the basic concept can be applied to many other fields. For example, the first and second needle apertures formed in the first and second upwardly extending arms are circular, since the medical needles for which it is designed have circular cross sections. However, the first and second apertures in the first and second upwardly extending arms need not have the same cross sectional geometry as the shaft, or other element, which is to be locked and passed through the first and second apertures. The requirement for locking is that when the first and second upwardly extending arms contact the shaft passing through the first and second apertures, the length of the first and second apertures perpendicular to the longitudinal axis of the shaft are less than the length of the cross sectional dimension of the shaft at that location. For example, the first and second apertures may be circular and the cross section of the shaft may be elliptical or any other geometry. Those skilled in the art will appreciate that the device described herein may be applied to all linkages that must be securely locked and easily unlocked for repositioning of the locked length of the shaft.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A needle stick protection device, comprising:
a housing;
a locking member positioned within the housing to permit the selective locking of the needle relative to the housing, the locking member comprising a substantially U-shaped spring biased strip having first and second upwardly extending arms biased relative to each other and connected by a central base member so as to define a spring biased strip with an open end, the first and second upwardly extending arms respectively including a first needle aperture and second needle aperture, wherein the locking member is coupled to at least one projection on a bottom of the housing to reduce finger pressure required in actuating the locking member;
a release member associated with the locking member for facilitating the controlled release of a needle locked in position by the locking member, the release member engaging the first upwardly extending arm and the second upwardly extending arm such that selective movement of the release member causes the first and second upwardly extending arms to move between a first locking position in which the first and second upwardly extending arms are angled relative to each other at either an oblique angle or an obtuse angle and a second release position in which the first and second upwardly extending arms are substantially parallel, the first and second upwardly extending arms being biased toward the first locking position;
wherein the release member includes a camming member having first and second sides shaped and dimensioned for respectively engaging camming surfaces of the first and second upwardly extending arms of the locking member; the release member further includes a release button coupled to the camming member, the release button extending through the housing for engagement by a user of the present needle stick protection device so as to permit a user to force the camming member downwardly toward the open end of the spring biased strip;
wherein the first and second needle apertures are oriented to permit the free passage of a needle therethrough when the locking member is in its second release position and the first and second needle apertures are oriented to lock the needle relative to the locking member when the first and second upwardly extending arms are in their first locking position.

2. The needle stick protection device according to claim 1, wherein the housing includes first and second apertures shaped and positioned for permitting the free passage of a needle through the housing.

3. The needle stick protection device according to claim 2, wherein the housing includes a tip shield extending adjacent the first aperture of the housing.

4. The needle stick protection device according to claim 2, further including a bellows seal extending adjacent the second aperture of the housing.

5. The needle stick protection device according to claim 1, wherein the locking member is a metallic strip biased toward the first locking position.

6. The needle stick protection device according to claim 1, wherein the locking member is positioned on a pair of pins.

7. The needle stick protection device according to claim 1, wherein the locking member is substantially delta shaped when in its first locked position.

8. The needle stick protection device according to claim 1, wherein the housing includes a tip shield.

9. The needle stick protection device according to claim 1, further including a bellows seal extending from the housing.

10. A syringe, comprising:

a syringe body having a needle extending therefrom;

a needle stick protection device selectively secured to the needle, the protection device including:

a housing;

a locking member positioned within the housing to permit the selective locking of the needle relative to the housing, the locking member comprising a substantially U-shaped spring biased strip having first and second upwardly extending arms biased relative to each other and connected by a central base member so as to define a spring biased strip with an open end, the first and second upwardly extending arms respectively including a first needle aperture and second needle aperture, wherein the locking member is coupled to at least one projection on a bottom of the housing to reduce finger pressure required in actuating the locking member;

a release member associated with the locking member for facilitating the controlled release of a needle locked in position by the locking member, the release member engaging the first upwardly extending arm and the second upwardly extending arm such that selective movement of the release member causes the first and second upwardly extending arms to move between a first locking position in which the first and second upwardly extending arms are angled relative to each other at either an oblique angle or an obtuse angle and a second release position in which the first and second upwardly extending arms are substantially parallel, the first and second upwardly extending arms being biased toward the first locking position;

wherein the release member includes a camming member having first and second sides shaped and dimensioned for respectively engaging camming surfaces of the first and second upwardly extending arms of the locking member; the release member further includes a release button coupled to the camming member, the release button extending through the housing for engagement by a user of the present needle stick protection device so as to permit a user to force the camming member downwardly toward the open end of the spring biased strip;

wherein the first and second needle apertures are oriented to permit the free passage of a needle therethrough when the locking member is in its second release position and the first and second needle apertures are oriented to lock the needle relative to the locking member when the first and second upwardly extending arms are in their first locking position.

11. The syringe according to claim 10, wherein housing includes first and second apertures shaped and positioned for permitting the free passage of a needle through the housing.

12. The syringe according to claim 11, wherein the housing includes a tip shield extending adjacent the first aperture of the housing.

13. The syringe according to claim 11, further including a bellows seal extending between the housing and the syringe body.

14. The syringe according to claim 10, wherein the locking member is a metallic strip biased toward the first locking position.

15. The syringe according to claim 10, wherein the locking member is positioned on a pair of pins.

16. The syringe according to claim 10, wherein the locking member is substantially delta shaped when in its first locked position.

17. The syringe according to claim 10, wherein the housing includes a tip shield.

18. The syringe according to claim 10, further including a bellows seal extending between the housing and the syringe body.

* * * * *